(12) United States Patent
Supinski

(10) Patent No.: US 6,875,214 B2
(45) Date of Patent: Apr. 5, 2005

(54) ROTATING TENDON ANCHOR

(76) Inventor: Robert S. Supinski, 3551 E. Groveland Rd., Mt. Morris, NY (US) 14510

( * ) Notice: Subject to any disclaimer, the term of this patent is extended or adjusted under 35 U.S.C. 154(b) by 0 days.

(21) Appl. No.: 10/390,105

(22) Filed: Mar. 17, 2003

(65) Prior Publication Data
US 2003/0176865 A1 Sep. 18, 2003

Related U.S. Application Data

(63) Continuation of application No. 09/668,993, filed on Sep. 25, 2000, now Pat. No. 6,579,295.

(51) Int. Cl.⁷ .............................................. A61B 17/56
(52) U.S. Cl. ...................................................... 606/72
(58) Field of Search .......................... 606/72, 60, 232; 623/13.14

(56) References Cited

U.S. PATENT DOCUMENTS

| | | | | |
|---|---|---|---|---|
| 4,669,473 A | * | 6/1987 | Richards et al. ............ | 606/215 |
| 4,823,794 A | * | 4/1989 | Pierce ........................ | 606/232 |
| 5,236,445 A | | 8/1993 | Hayhurst et al. | |
| 5,282,802 A | | 2/1994 | Mahoney, III | |
| 5,403,348 A | * | 4/1995 | Bonutti ...................... | 606/232 |
| 5,443,509 A | | 8/1995 | Boucher et al. | |
| 5,464,425 A | * | 11/1995 | Skiba ......................... | 606/232 |
| 5,632,748 A | | 5/1997 | Beck, Jr. et al. | |
| 5,707,395 A | | 1/1998 | Li | |
| 5,709,695 A | * | 1/1998 | Northrup, III .............. | 606/148 |
| 5,709,708 A | * | 1/1998 | Thal ........................... | 606/232 |
| 5,904,704 A | | 5/1999 | Goble et al. | |
| 5,906,624 A | | 5/1999 | Wenstrom, Jr. | |
| 5,931,869 A | | 8/1999 | Boucher et al. | |
| 5,944,724 A | | 8/1999 | Lizardi | |
| 5,961,538 A | * | 10/1999 | Pedlick et al. .............. | 606/232 |
| 6,024,758 A | * | 2/2000 | Thal ........................... | 606/232 |
| 6,086,591 A | * | 7/2000 | Bojarski ..................... | 606/64 |
| 6,143,017 A | * | 11/2000 | Thal ........................... | 606/232 |
| 6,264,694 B1 | | 7/2001 | Weiler | |
| 6,293,950 B1 | * | 9/2001 | Lynch et al. ................ | 606/77 |
| 6,682,549 B2 | * | 1/2004 | Bartlett ....................... | 606/232 |
| 6,730,112 B2 | * | 5/2004 | Levinson .................... | 606/232 |
| 2002/0040241 A1 | | 4/2002 | Jarvlnen | |

OTHER PUBLICATIONS

Brochure entitled "Bone Mulch Screw/Washerloc Device–For the New Millennium" demonstrating surgical technique and Stephen M. Howell, M.D. Arthroteck@2000–pg. 1, Line 25.

* cited by examiner

Primary Examiner—Eduardo C. Robert
(74) Attorney, Agent, or Firm—Thomas R. Shaffer, Esq.

(57) ABSTRACT

A tendon anchor is used for attaching a tendon to a bone without sutures within a cylindrical bore drilled into the bone. The tendon anchor is adapted for insertion into the bore of a bone and has a generally elongated rectangular shape with opposite ends thereon. The tendon anchor has a transverse hole therein adapted to receive a central portion of the tendon and when the tendon anchor (with a tendon threaded into the hole therein) is inserted in the bore in the bone longitudinally, exerting force upon the ends of the tendon causes the tendon anchor to rotate to a partially transverse position within the bore thus forcing opposite end portions of the anchor into engagement with the cylindrical bore in the bone thereby securing the tendon in the bone.

2 Claims, 8 Drawing Sheets

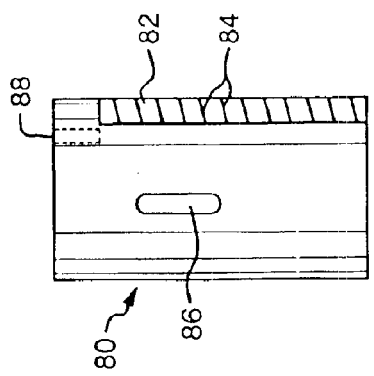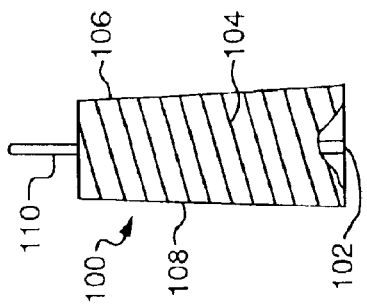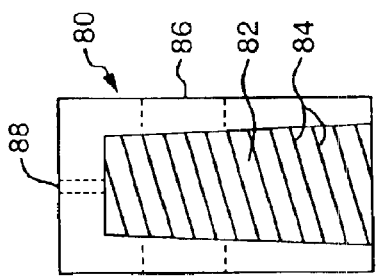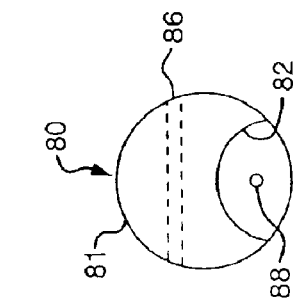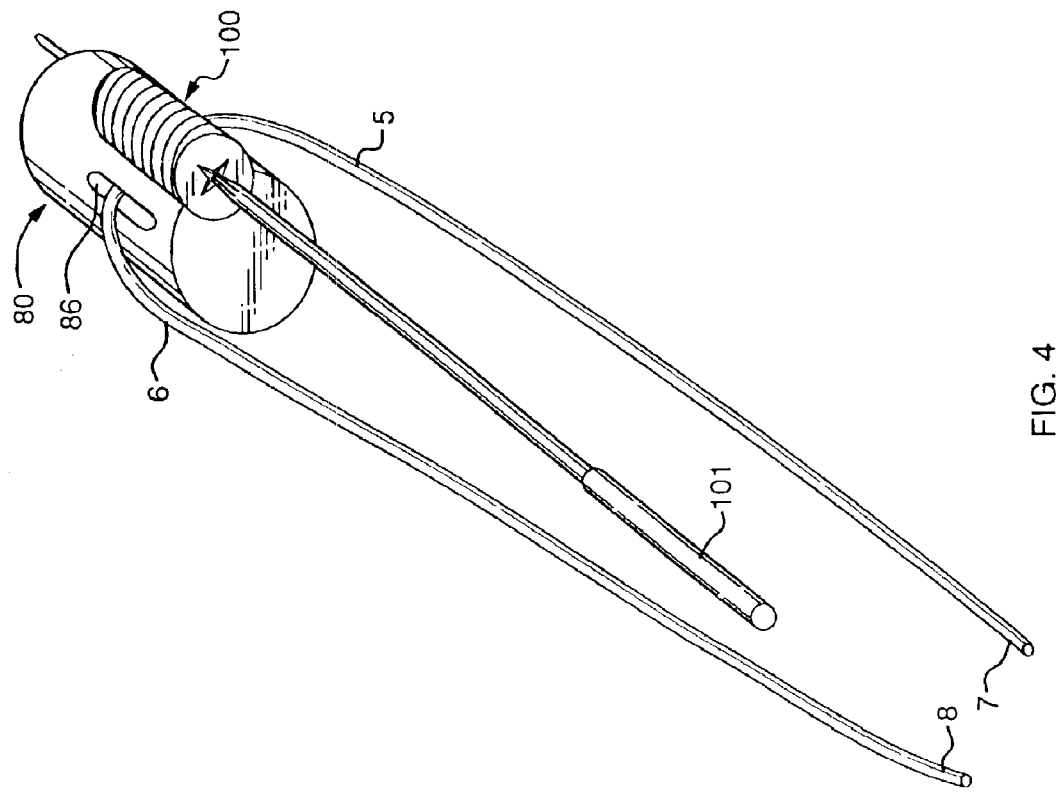

ROTATING TENDON ANCHOR

The present application is a continuation of U.S. Patent Application of Robert S. Supinski for "Tendon Anchors", U.S. Ser. No. 09/668,993, filed Sep. 25, 2000 now U.S. Pat. No. 6,579,295.

BACKGROUND OF THE INVENTION

1. Field of the Invention

The present invention relates to tendon anchors. More specifically, it relates to tendon anchors utilized to attach tendons to one or more bones without sutures and through a single bore drilled into the bone.

2. Description of the Prior Art

The need to effectively and efficiently attach a tendon to a bone is absolutely critical in a number of orthopedic surgical procedures. The most common current practice is to utilize a device called a suture anchor to attach a suture to the bone and thereafter tie the tendon to the suture thereby making the attachment of the tendon to the bone. Examples of this practice are set forth in U.S. Pat. Nos. 5,961,538; 5,944,724; 5,906,624; and 5,904,704. While such techniques are reasonably effective, the use of suture anchors is overly time consuming and creates unnecessary risks of failure. For example, the suture may become detached from the anchor or the tendon and the process of suturing the tendon to the anchor may actually weaken the strength of the tendon itself or cause it to tear. It is believed that a better technique would involve a direct attachment of the tendon itself to a tendon anchor which is secured within the bone.

One known process which is believed to be a step in the right direction is disclosed in a publication entitled "Bone Mulch Screw/WasherLoc Device For the New Millennium" published by Arthrotek, a Biomet Company. The publication is undated but is believed to have been published in early 2000 and not earlier than the later part of 1999. This publication discloses an ACL reconstruction technique in which a tendon is ultimately attached directly to the bone by means of tendon anchors. While sutures are not utilized to attach the tendon to the bone, the process still requires the use of a suture (pp. 9–10) attached to one end of the tendon to pull the tendon over a transverse cross beam of the femoral anchor. Such a process is overly complex and unnecessarily time consuming.

Further, the Arthotek device itself is overly complex and utilizes at least one tendon anchor which requires drilling two separate bores into the femur, one longitudinally through which the tendon is threaded and one transversely to provide a cross beam over which the tendon is passed (see FIG. 25 of publication). Drilling an extra bore into the bone takes more time, requires precision to make certain that the two bore holes intersect, causes increased trauma to the patient and can weaken the overall structure of the bone. Thus, while this technique provides an improvement over prior art devices which require suturing a tendon to a suture anchor (sometimes called bone anchor), there remains a need for a simple, easy to install tendon anchor which does not require sutures at all during the installation procedure and which only require the drilling of a single bore into the bone.

IN THE SUMMARY OF THE INVENTION

The present invention meets this need by providing a number of differently designed tendon anchors which each include a channel to receive and hold a tendon which is inserted into a single bore in the bone with the anchor. Thus, no sutures are required and only a single bore hole is needed.

In its simplest form, the present invention provides a tendon anchor for attaching a tendon to at least one bone without sutures within a bore drilled into said at least one bone comprising a first tendon, anchor adapted for insertion into said bore of a first bone, said first tendon anchor having a channel provided therein for receiving and holding a central portion of a tendon during insertion and when in final position in the bore of said first bone with opposite ends of the tendon extending out of the singular bore; and a first securing means associated with said first tendon anchor for moving at least a part of the first tendon anchor radially outward to securely engage the first tendon anchor and the central portion of the tendon to the first bone by urging at least a part of the first tendon anchor against a cylindrical wall portion of said bore in said first bone.

Preferably, said first tendon anchor is generally cylindrical in shape with a cylindrical outer wall and has a crescent shaped recess therein, said recess extending longitudinally along a cylindrical wall portion thereof from one end portion of the first tendon anchor to a location at least two-thirds of the distance toward an opposite end portion thereof.

Preferably, said first securing means is a first tapered screw adapted to be received between a cylindrical wall of the bore in said first bone and said threaded recess, whereby tightening said first screw causes one side of the first screw to embed itself into a cylindrical wall of the bore and an opposite side of the first screw urges a portion of the first tendon anchor opposite said crescent shaped recess and the entire tendon anchor radially outward against an opposite cylindrical wall of the bore.

In a presently preferred embodiment of the invention, said cylindrically outer wall portion of said first anchor means is provided with outward projections thereon to aid in engaging said outer wall portion of the first tendon anchor to the cylindrical wall of the bore.

Preferably, said cylindrically shaped first tendon anchor has a transverse hole therein which forms said channel, said transverse hole extending from opposite cylindrical walls and positioned transversely to the crescent shaped recess and wherein said tendon is threaded through said transverse hole whereby a central portion thereof is positioned within said transverse hole.

In many cases, the invention will utilize two tendon anchors. In such cases, a second tendon anchor is provided which is adapted for insertion into a bore drilled into a second bone; and a second securing means associated with said second tendon anchor for moving at least a part of the second tendon anchor radially outward to securely engage the second tendon anchor and the end portions of the tendon to the second bone by urging at least a part of the second tendon anchor against a cylindrical wall portion of said bore in said second bone.

Preferably, said second tendon anchor is also generally cylindrical in shape with a cylindrical outer wall and has a crescent shaped recess therein, said recess extending longitudinally along and entire cylindrical wall portion thereof from one end portion of the second tendon anchor to an opposite end portion thereof.

Preferably, said second securing means is a second tapered screw adapted to be received between a cylindrical wall of the bore in said second bone and said threaded recess, whereby tightening said second screw causes one side of the second screw to embed itself into a cylindrical wall of the bore in the second bone and an opposite side of the second screw urges a portion of the second tendon anchor opposite said crescent shaped recess and the entire second tendon anchor radially outward against an opposite cylindrical wall of the bore in said second bone.

In the preferred embodiment, said cylindrically outer wall portion of said second anchor means is provided with outward projections thereon to aid in engaging said outer wall portion of the second tendon anchor to the cylindrical wall of the bore of the second bone.

Preferably, said cylindrically shaped second tendon anchor has notches therein to receive the opposite ends of said tendon and said ends of said tendon are compressed and held in place between the cylindrical wall of the bore of the second bone and said cylindrical outer wall of the second tendon anchor.

In an alternative embodiment of the invention, said first tendon anchor has a generally elongated rectangular shape with opposite ends thereof having engaging portions thereon adapted to engage into the cylindrical wall of the bore in the first bone, said first tendon anchor having a securing means in the form of a transverse hole therein adapted to receive a central portion of said tendon, said hole also constituting said channel, said hole being closer to one end of the first tendon than the other anchor and closer to one side of the tendon anchor than the other, whereby said first tendon anchor with a tendon threaded into said hole therein is inserted into the bore in the first bone longitudinally and upon exerting force upon the ends of the tendon, said first tendon anchor rotates to a partially transverse position within the bore thus forcing said engaging portions into the cylindrical bore in the first bone thereby securing the tendon in said first bone.

In yet another embodiment of the invention, said first tendon anchor is formed of a first elongated member and a second elongated member, said first and second members each having an engaging portion on at least one end thereof adapted to engage into the cylindrical wall of the bore in the first bone, said first and second members having a channel provided in one end thereof for receiving and holding a central portion of a tendon during insertion and when in final position in the bore in said first bone, said first and second elongated members engaging one another at a location intermediate the end portions thereof and adapted to move relative to one another in a scissor like fashion whereby said members are inserted into the bore of the first bone in a substantially closed scissor position with the central portion of the tendon engaged and held in the channel of each member and whereby exerting force upon the ends of the tendon causes the members to move to an open scissor position forcing the engaging portion of each member into the cylindrical bore in the first bone thereby securing the tendon in said first bone.

In this embodiment, exerting greater force on the tendon ends causes said engaging portion to embed more deeply into the cylindrical bore in the first bone thereby more securely holding the tendon in said first bone.

BRIEF DESCRIPTION OF THE DRAWINGS

FIG. 4 is a perspective view of the presently preferred first tendon anchor with the securing means in the form of a threaded screw attached and also showing a screw driver and the tendon.

FIG. 5 is a front plan view of the presently preferred first tendon anchor of the present invention.

FIG. 6 is a side plan view of the presently preferred first tendon anchor of the present invention.

FIG. 7 is a top plan view of the presently preferred first tendon anchor of the present invention.

FIG. 8 is a side plan view of the presently preferred first securing means of the present invention.

DETAILED DESCRIPTION OF THE PREFERRED EMBODIMENTS

Referring to the figures, the presently preferred embodiments of the present invention will be described in connection with an ACL reconstruction. While this detailed description relates to the attachment of a tendon between a femur and a tibia bone located within the knee of a patient, it is to be understood that the invention is not limited thereto. A similar tendon anchor could be utilized to secure a tendon to any bone within the human body.

Figure 1:
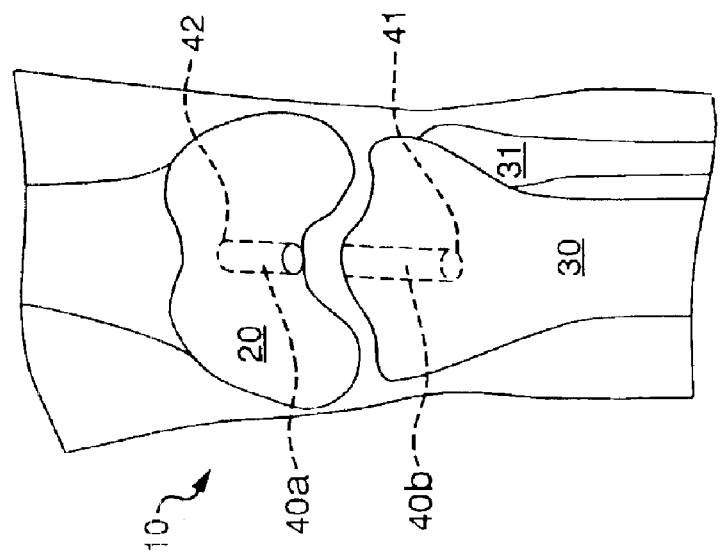
FIG. 1 is a perspective view of a human knee having a single bore hole drilled therein.

Referring to FIG. 1, a human knee 10 is shown. A femur bone 20, a tibia bone 30 and a fibia bone 31 are shown. A singular bore hole 40a, 40b is drilled into the knee beginning at point 41 in the tibia and ending at point 42 in the femur. Thus, a singular drilling action is utilized to drill through both the tibia and the femur.

Figure 3:
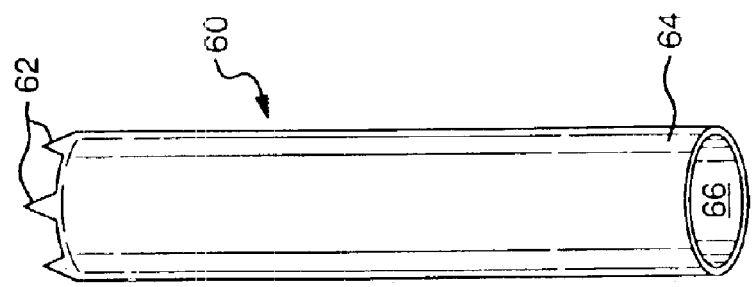
FIG. 3 is a perspective view of a hollow guide tube adapted to be tapped into the bones guided by said solid inserter rod.
Figure 2:
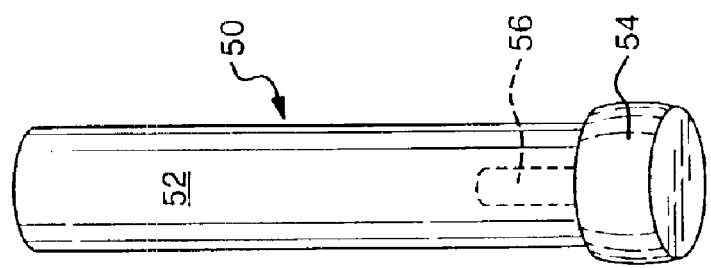
FIG. 2 is a perspective view of a solid inserter rod adapted for insertion into said single bore hole.

Once the tibial tunnel 40b and femoral tunnel 40a are created by techniques which are well known in the field, end 52 of a solid inserter rod 50 (FIG. 2) is tapped into the tibial tunnel 40b and femoral tunnel 40a. The inserter rod 50 includes a removable head 54 which is screwed into the inserter at location 56. It will be obvious that by merely twisting end 54 relative to rod 50, end 54 may be removed from the rod 50. Once the solid inserter rod is tapped completely into the tibial tunnel 40b and femoral tunnel 40a, the inserter rod end 54 is removed and a hollow guide tube 60 (FIG. 3) beginning with end 62 thereof is tapped over the rod 50 into position within the tibial tunnel 40b and femoral tunnel 40a. The hollow guide tube is tapped at end 64 thus causing the projections 62 to embed themselves into the bone at end 42 of the femoral tunnel 40a. Once the hollow guide tube is inserted, the screw end 54 is screwed into the solid rod 50 and solid rod 50 is removed from the tibial tunnel 40b and femoral tunnel 40a.

Once the hollow guide tube is properly inserted, the assembly shown in FIG. 4 is inserted within the interior 66 (FIG. 3) of the hollow guide tube 60. This assembly includes a first tendon anchor 80 (which is shown in FIGS. 4 through 7) and a securing means 100 in the form of a threaded screw (which is shown in FIGS. 4 and 8) as well as a tendon 5 which has a central portion 6 and end portions 7 and 8. A long handled screwdriver 101 is shown inserted into the first securing means 100. It is noted that the tendon 5 is threaded through a hole 86 provided in the first tendon anchor. The tendon is threaded through hole 86 prior to insertion in the guide tube.

As can be seen in FIGS. 4 through 7, the first tendon anchor has a crescent shaped recess 82 provided therein which has external threads 84 which are adapted to mesh with threads 104 of screw 100. It is noted that the crescent shaped recess does not extend the whole length of the anchor means but that a small guide pin hole 88 does extend completely through the first tendon anchor 80. The guide pin hole 88 is positioned to receive a guide pin 110 which is attached to the entry end of screw 100. The opposite end 102 of screw 100 is provided with receiving means to receive the end of a screw driver 101.

Once the assembly of FIG. 4 is inserted within the guide tube 60 to the end 42 of the femoral tunnel 40a, the guide tube 50 is withdrawn and the screw 100 is tightened. Because screw 100 is tapered as best shown in FIG. 8, this causes the outer surface 81 of the first tendon anchor to be pushed radially outward into the femoral tunnel engaging it against the femoral tunnel. Likewise, one side 106 of the screw member 100 will engage itself in an opposite side of the femoral tunnel 40a. Once fully tightened, screw driver 101 is removed from the tibial tunnel 40b and femoral tunnel 40a thereby leaving tendon ends 7 and 8 extending out of the opening 41 of the tibial tunnel 40b.

Figure 9:
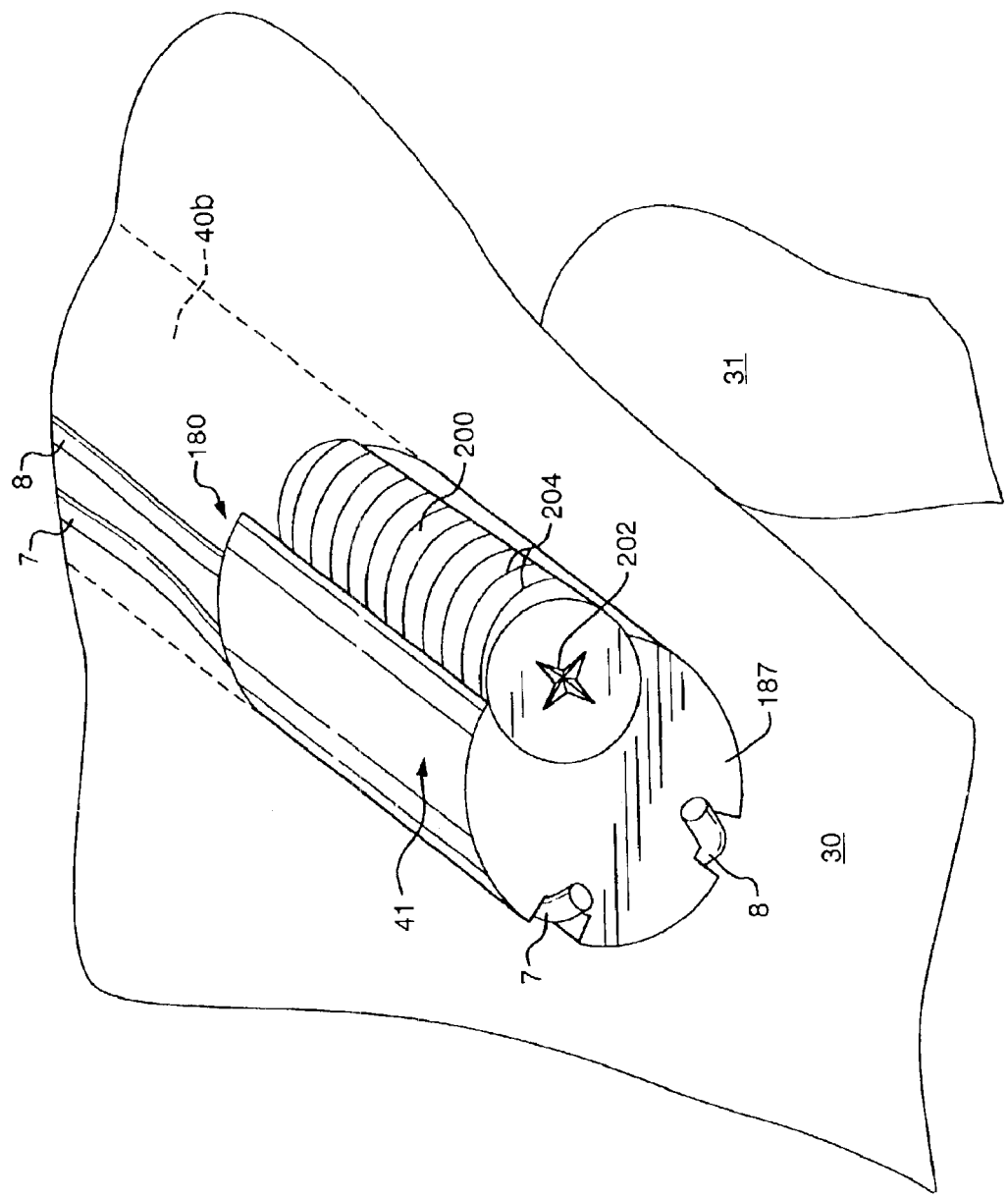
FIG. 9 is a perspective view of the presently preferred second tendon anchor with the second securing means in the form of a threaded screw attached in a second bone and also showing the ends of a tendon.
Figure 12:
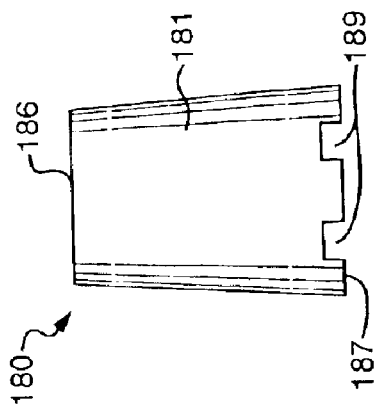
FIG. 12 is a rear plan view of the presently preferred second tendon anchor.
Figure 11:
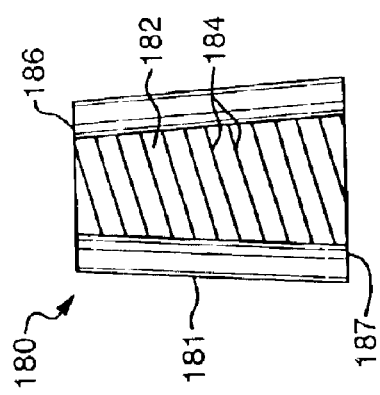
FIG. 11 is a front plan view of the presently preferred second tendon anchor.
Figure 10:
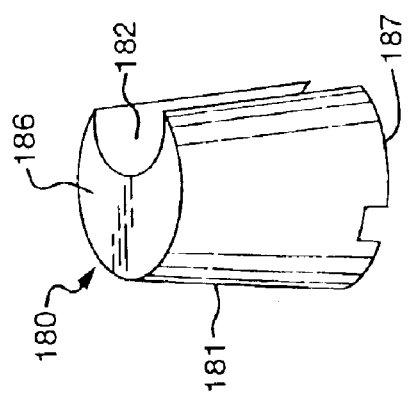
FIG. 10 is a perspective view of the presently preferred second tendon anchor.

Referring to FIGS. 9 through 12, a second tendon anchor is shown and described. This tendon anchor is similar in principle to the first tendon anchor but differs slightly in structure. As shown in FIG. 9, the second tendon anchor 180 is shown as positioned within end 41 of the tibial tunnel 40b. Ends 7 and 8 of the tendon extend out of the tibial tunnel and are secured against the wall of the tibial tunnel by outside surface 181 of the second tendon anchor 180. As shown in FIGS. 9, 10 and 11, a crescent shaped recess 182 is provided in the second tendon anchor which extends the full length of the tendon anchor. As with the first tendon anchor, second tendon anchor 184 has threads 184 provided in the recess 182 which are adapted to mesh with threads 204 of screw 200 (which constitutes the second securing means). Screw 200 is adapted for insertion by means of a screw driver which enters the recess at 202. As best shown in FIGS. 10, 11 and 12, the second tendon anchor 180 is tapered with insertion end 186 being smaller in diameter than outer end 187. It is also noted that notches 189 are provided in the outer end 187 for securely holding the ends 7 and 8 of tendon 5 in a desired position. The ends 7 and 8 of tendon 5 may then be trimmed once the screw 200 is fully engaged. As with the first tendon anchor, tightening the screw 200 forces outer surface 181 radially outward into the end 41 of the tibial tunnel 40b.

Figure 14:
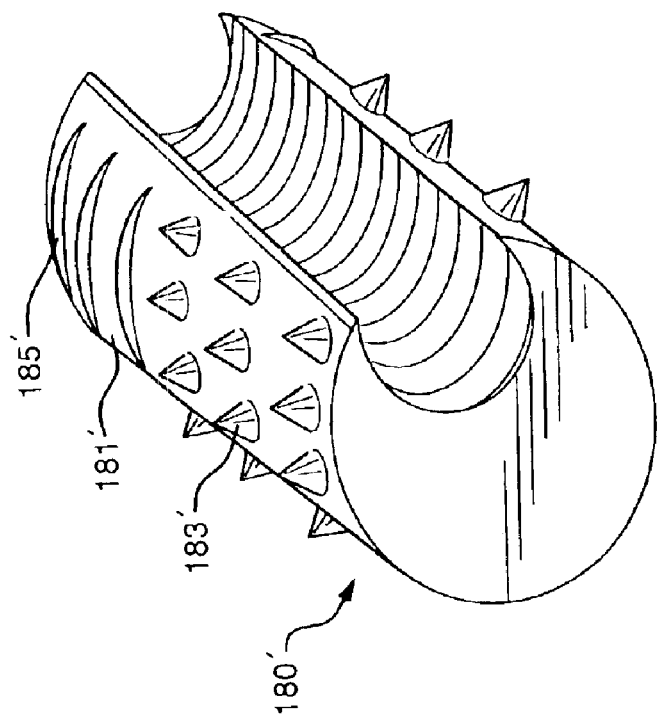
FIG. 14 is a perspective view of a second tendon anchor having projections on an outer surface thereof in the form of teeth and threads.
Figure 13:
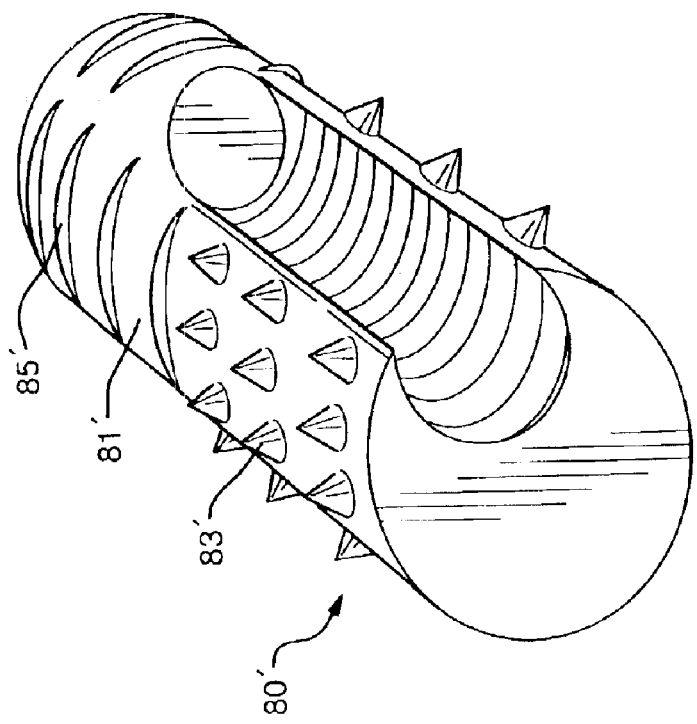
FIG. 13 is a perspective view of a first tendon anchor having projections on an outer surface thereof in the form of teeth and threads.
Figure 18:
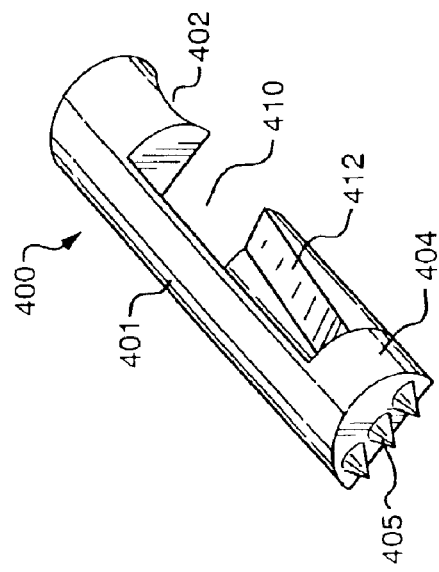
FIG. 18 is a perspective view of one member of an alternative embodiment of a first tendon anchor which comprises two identical members from a different perspective.
Figure 17:
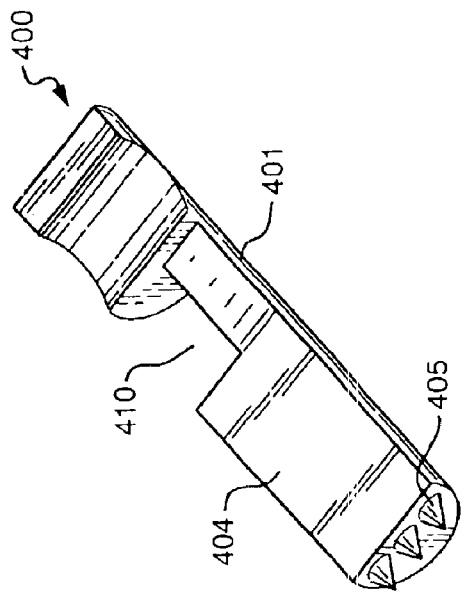
FIG. 17 is a perspective view of one member of an alternative embodiment of a first tendon anchor which comprises two identical members.

FIGS. 13 and 14 are provided to show that it is preferable to provide some type of projections on the outer surface 81' and 181' of the first tendon anchor 80' and the second tendon anchor 180'. These projections may take the form of teeth 81' and 183' or in the form of threads or ridges as shown at 85' and 185'. It will be obvious to the reader that these projections 81', 85', 183' and 185' are designed to engage into the bone of the femoral tunnel 40a and tibial tunnel 40b.

Figure 19:
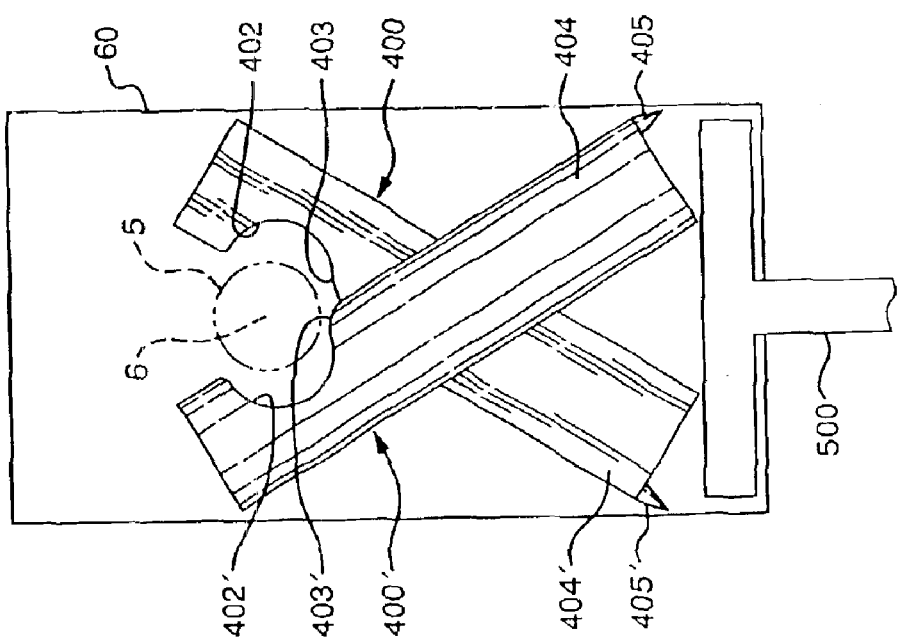
FIG. 19 is a side elevational view showing both members of an alternative first tendon anchor which comprises two identical members in a closed scissor position.

FIGS. 15 through 19 show an alternative embodiment of a first tendon anchor according to the present invention. In this embodiment, as best shown in FIG. 19, two identical members 400 and 400' are provided. The details of the members 400 and 400' are identical and thus only one of such members will be described in detail. Essentially, the members 400 and 400' act like a pair of scissors and are adaptable for rotation between a closed scissor position and an open scissor position by downward force on ends 7 and 8 of the tendon 5. Pulling downward on ends 7 and 8 causes the central portion 6 of tendon 5 to exert force on the members 400 and 400' thus opening the members causing engaging means 405 and 405' to engage within the femoral tunnel 40a.

Figure 15:
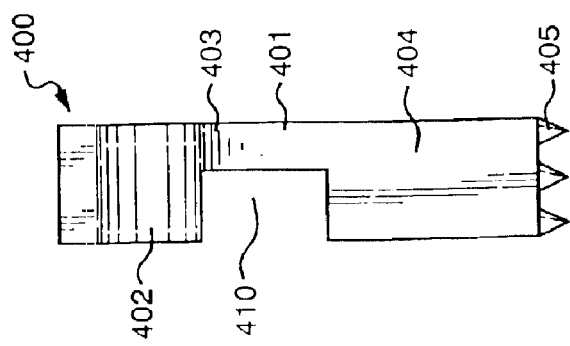
FIG. 15 is a front plan view of one member of an alternative embodiment of a first tendon anchor which comprises two identical members.

Referring to FIGS. 15 through 18, the details of the member 400 (and 400') will be described. Essentially, member 400 is in the form of a cylindrical body which has been cut longitudinally in half. FIG. 15 shows a front view of member 400 which is essentially flat. Member 400 includes a main body portion 401 into which a notch 410 is provided. This notch is to allow for the mating of an identical member 401' and to allow a scissor action to occur. Also provided on the flat surface as shown in FIG. 15 is a channel 402 which is adapted to initially receive and hold the central portion 6 of a tendon 5 during insertion. It is noted that the channel 402 includes a ramp like surface 403 which facilitates opening of the members upon the downward force of the central portion 6 of a tendon.

Figure 16:
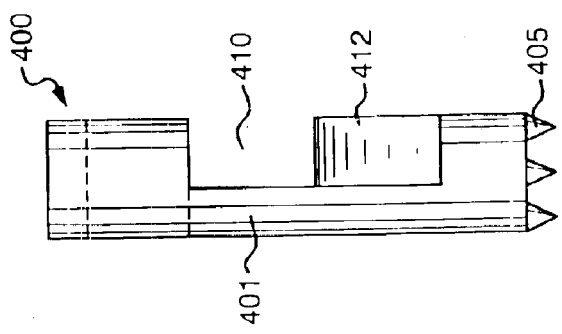
FIG. 16 is a rear plan view of one member of an alternative embodiment of a first tendon anchor which comprises two identical members.

FIG. 16 shows the rear of the member 400 with similar parts shown. An inclined surface 412 is provided which essentially allows the members to open more widely. Engaging teeth 405 are provided at end 404 of the member.

Figure 20:
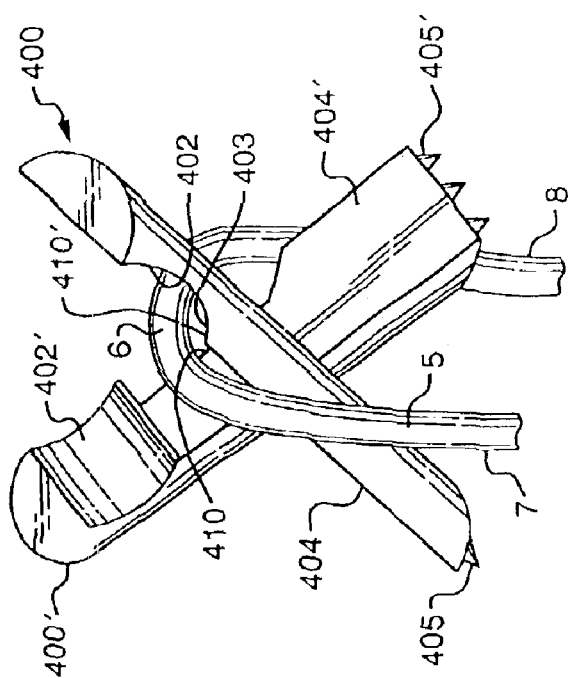
FIG. 20 is a perspective view showing both members of an alternative first tendon anchor which comprises two identical members in an open scissor position.

FIG. 19 shows the members 400 and 400' in a closed scissor position with the tendon 5 being held within the channels 402 and 402'. The assembly as shown in FIG. 19 is inserted within the hollow guide tube 60 and is pushed by a push member 500 into the femoral tunnel to end 42 thereof. The hollow guide tube member 60 is then withdrawn. Upon a pulling action of ends 7 and 8 which extend outside of the end 41 of the tibial tunnel 40b, causes the members 400 and 400' to rotate to an open scissor position as shown in FIG. 20. This causes the engaging teeth 405 and 405' to engage within the cylindrical wall of the femoral tunnel 40a securing the anchor firmly in the desired position. It is noted because of the mechanics involved that the greater the tension on ends 7 and 8, the greater the outward force of ends 404 and 404' thus providing greater resistance and a stronger resistance to pull out of the anchor.

It will be obvious to the reader that the process of simply inserting the assembly into a hollow guide tube 60 as shown in FIG. 19, removing the tube and simply pulling on the ends 7 and 8 to engage the anchor is a far faster and far simpler device than has been heretofore proposed.

Figure 22:
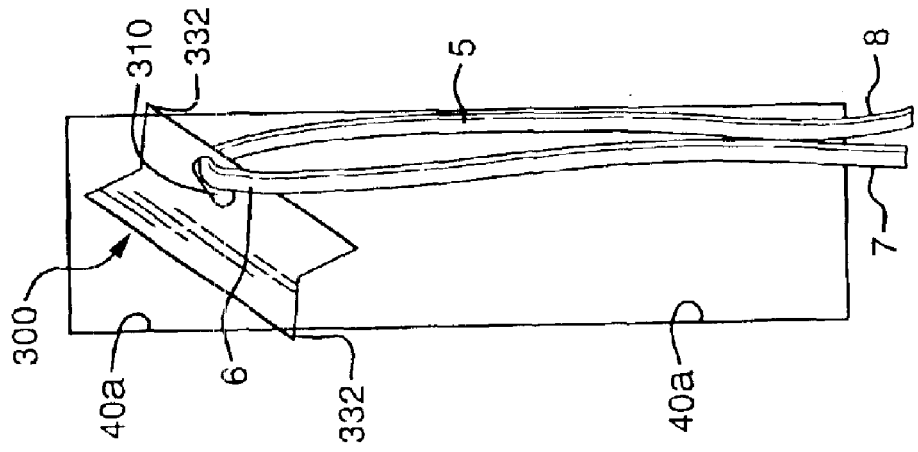
FIG. 22 is a side elevational view showing of yet another alternative embodiment of a first tendon anchor which shows the anchor in a transverse engaging position.
Figure 21:
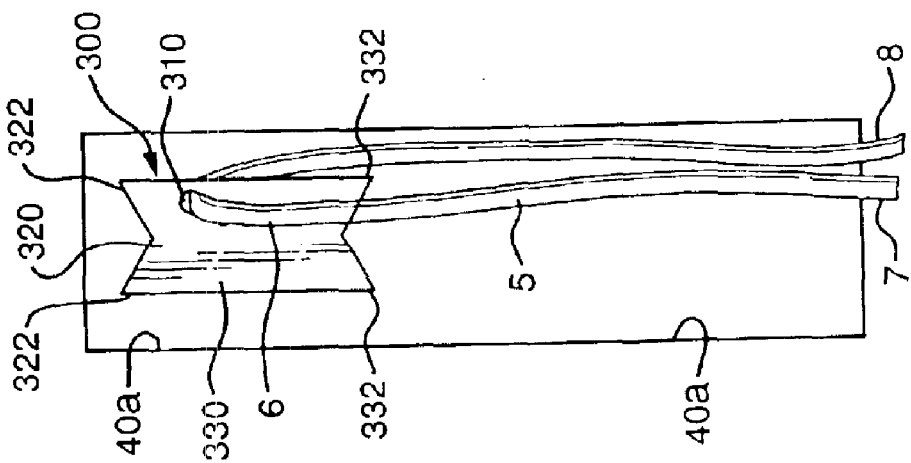
FIG. 21 is a side elevational view showing yet another alternative embodiment of a first tendon anchor which shows the anchor in a vertical insertion position.

FIGS. 21 and 22 show yet another embodiment of a first tendon anchor 300. The tendon anchor 300 is generally rectangular in shape and has engaging teeth portions provided at the corners 322 thereon. An opening 310 is provided through the first tendon anchor member 300 at a location in the top right quadrant as shown in FIG. 21. The opening 310 is in the form of a hole which is located closer to one end (a hole end) than to an opposite end and is located closer to one side (a hole side) than to an opposite side. By having the opening 310 above the center of the rectangular member and off the longitudinal axis thereof, the location of the hole facilitates a rotation of the member within the femoral tunnel 40*a*. The device is positioned longitudinally for insertion as shown in FIG. 21 and may be pushed into position in much the same manner as the device described with respect to FIG. 19. Once in position, merely pulling the ends 7 and 8 of the tendon 5 downwardly causes the first anchor member 300 to rotate from a longitudinal position to a transverse position with corner teeth 322 and 332 engaging the cylindrical wall of the femoral tunnel 40*a*. While the particular operation of this tendon anchor is superficially similar to a device shown in FIG. 10 of U.S. Pat. No. 5,961,538, it is noted that this device clearly does not anticipate nor teach the provision of a channel for adapting to receive a tendon. Rather, that device relies upon the prior art method of using sutures to sew the tendon in place.

To briefly review the operation of all of the tendon anchor devices described herein, the process simply involves the drilling of a tunnel (in the example shown into the tibia and fibia of the knee), passing a solid rod into the tunnel thus created, impacting the hollow guide tube over the solid rod and removing the solid rod, inserting the anchor/screw driver through the tibial tunnel into the femoral tunnel, removing the outer sheath, and either tightening the securing means or simply pulling the ends of the tendon to engage the securing means. Finally, a second tendon anchor means in the form of a tibial plug is provided and screwed into the tibial tunnel.

It is noted that the tendon anchors described herein may be made from any suitable bio-compatible metal, absorbable materials or from bone/allograft.

It is anticipated that the present invention can be utilized with any form of tendon be the same harvested from the hamstring or be it artificial.

While I have shown and described the presently preferred embodiment of my invention, the invention is not limited thereto and may be otherwise variously practiced within the scope of the following claims:

I claim:

1. A tendon anchor for attaching a tendon to at least one bone without sutures within a cylindrical bore drilled into said at least one bone comprising a tendon anchor adapted for insertion into said bore of a bone, said tendon anchor having a generally elongated rectangular shape with opposite ends thereon, each of said opposite ends of said tendon anchor having an engaging portion thereon adapted to engage a cylindrical wall of the bore in the bone, said tendon anchor having a transverse hole therein, said transverse hole located closer to a hole end of said tendon anchor than to an opposite end thereof and said hole located closer to a hole side of the tendon anchor than to an opposite side thereof, through which transverse hole a central portion of said tendon is received whereby when said tendon anchor with a tendon threaded into said hole therein is inserted in the bore in the bone longitudinally, exerting force upon the ends of the tendon solely causes said hole end of said tendon anchor to rotate toward said hole side to a partially transverse position within the bore thus forcing said opposite end portions into engagement with the cylindrical bore in the bone thereby securing the tendon in said bone.

2. A tendon anchor according to claim 1 wherein said engaging portion further comprises a recessed portion in a middle portion of each said end and a pair of triangular extensions along each side of each said end.

\* \* \* \* \*